United States Patent
Larsson et al.

(10) Patent No.: US 6,667,800 B1
(45) Date of Patent: *Dec. 23, 2003

(54) METHOD AND DEVICE FOR MEASURING AND QUANTIFYING SURFACE DEFECTS ON A TEST SURFACE

(75) Inventors: Peter Larsson, Västra Frölunda (SE); Anders Larsson, Göteborg (SE); Erland Max, Västra Frölunda (SE)

(73) Assignee: Volvo Car Corporation, Göteborg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/375,848

(22) Filed: Aug. 17, 1999

Related U.S. Application Data

(63) Continuation of application No. PCT/SE98/00226, filed on Feb. 10, 1998.

(30) Foreign Application Priority Data

Feb. 17, 1997 (SE) ................................................ 9700539

(51) Int. Cl.⁷ ............................................. G01N 21/00
(52) U.S. Cl. .................................................... 356/237.2
(58) Field of Search ................................ 356/376, 237, 356/375, 237.2, 369, 338, 430, 600–624, 394, 371; 382/141–149, 274, 270

(56) References Cited

U.S. PATENT DOCUMENTS

| 4,162,126 | A |   | 7/1979  | Nakagawa et al. |
|-----------|---|---|---------|-----------------|
| 4,920,385 | A |   | 4/1990  | Clarke et al.   |
| 4,980,993 | A | * | 1/1991  | Umezaki         |
| 5,129,009 | A | * | 7/1992  | Lebeau ................... 382/8 |
| 5,426,506 | A |   | 6/1995  | Ellingson et al. |
| 5,828,500 | A | * | 10/1998 | Kida et al.     |
| 5,859,698 | A | * | 1/1999  | Chau et al.     |
| 5,987,159 | A | * | 11/1999 | Nichani         |

FOREIGN PATENT DOCUMENTS

WO           9004166        4/1990

* cited by examiner

*Primary Examiner*—Tu T. Nguyen
(74) *Attorney, Agent, or Firm*—Howrey Simon Arnold & White LLP

(57) ABSTRACT

Method and apparatus for measuring and quantifying surface finishing defects on a coated opaque test surface including utilizing at least one light source, at least one camera, and a central unit that has image analysis capability. At least two partial images are recorded with the camera while illuminating the opaque test surface using the light source. The two partial images are produced from the test surface by differing the angle of incident light for different partial images. The two partial images are processed by the central unit thereby establishing a difference image that is analyzed to quantify the degree of surface finishing defects on the coated opaque test surface. Optionally, the central unit further has operational control capabilities over at least one of the light sources and camera.

18 Claims, 2 Drawing Sheets

METHOD AND DEVICE FOR MEASURING AND QUANTIFYING SURFACE DEFECTS ON A TEST SURFACE

RELATED PATENT APPLICATIONS

This is a continuation patent application of International Application No. PCT/SE98/00226 filed Feb. 10, 1998 that designates the United States. The full disclosure of said application, in its entirety, is hereby expressly incorporated by reference into the present application.

DESCRIPTION

Technical Field

The present invention relates to a method and a device for measuring and quantifying surface defects, such as defects on polished surfaces, by means of optical registration with subsequent image analysis and image processing.

The method and the device according to the invention are primarily applicable for measuring and quantifying surface defects in the form of so-called polishing roses, which may arise in connection with polishing of, for example, painted sheet metal details within the motor car industry. The method and the device according to the present invention may also be utilized, however, for other similar applications, for example in connection with quality control of rubbing or grinding processes.

In this context, the expression "polishing roses" refers to a certain type of surface defects which have arisen during polishing or other similar surface finishing, such as rubbing or grinding. The polishing roses may adopt several different shapes, depending on the circumstances under which they have arisen.

The method practiced by means of the device according to the present invention may replace the manual, visual examination process which has been previously used for quality testing and assessment of surface defects, such as polishing roses, within applications where a painted surface with a smooth and glossy surface finish is required.

BACKGROUND OF THE INVENTION

Within the vehicle manufacturing industry (motor car. industry), ever increasing demands are made today on the quality of the end product, something which has resulted in the use of more and more advanced systems for quality testing and control.

As is well-known to persons skilled in the art, a modern passenger car or truck consists of a plurality of components which originate from different production lines, or from different manufacturers, and which are assembled in a step-by-step process into a vehicle.

Some of these components have painted sheet metal components which, in the case of visible body components, generally are polished in order to achieve a smooth and glossy surface finish. In certain cases, it may also happen that components made at least partially of polymeric materials (different plastics) are polished for the same reason.

Independent of the stage one has reached in the assembly process, the need sometimes arises for testing of the polishing result of a component which has been polished in an earlier step.

Also in connection with product or process development, there is a need to be able to test or evaluate surface finishing results. Such an evaluation may serve as a guide in the choice of, for example, surface finishing equipment, polishing equipment or polishing technique.

Also when developing new paints and car enamels, it is of great importance to be able to identify and eliminate those paints and enamels in which polishing roses frequently arise.

Before the present invention, such quality testing of polished surfaces has in principle been done by means of manual, visual assessment of polished test specimens or finished polished components or vehicles.

One great disadvantage with such manual, visual assessment of the polishing result has been that it is dependent on the individual, i.e. only experienced staff with many years of experience from practicing such assessment are been able to accurately perform such evaluation.

Another disadvantage has been that the assessment results have not been reproducible or quantifiable. Furthermore, such results to a great extent have been dependent on the light conditions at the testing station. The manual, visual assessment of the polishing result has until this time been most advantageously accomplished outdoors and in brilliant sunshine.

A frequently occurring surface defect which may arise in connection with surface finishing of different components is so-called polishing roses. As mentioned earlier, in this context polishing roses refer to certain types of surface defects which have arisen during polishing or other similar surface finishing such as rubbing or grinding processes. The polishing roses may adopt several different forms, depending on conditions under which they have arisen.

Accordingly, a typical form of polishing rose manifests itself as a so-called holographic image. In this case, the holographic image may be described as a situation in which an image or pattern appears to be situated below the plane of a polished surface when it is observed from one direction, and the same image appears to be situated above the plane of the polished surface when that surface is observed from an opposite direction.

Another frequently occurring form of polishing rose manifests itself as a blurred polishing pattern in the surface when the surface is observed from above. Such a blurred polishing pattern usually appears together with polishing roses of the earlier-mentioned type, i.e. holographic images.

A third form in which polishing roses occur is sharp, thin scratches, which are clearly visible when the angle of observation is perpendicular to the scratches. This form of polishing rose may appear alone, or together with polishing roses of the two above-mentioned types.

Common to all different forms of polishing roses is that they are practically invisible during normal lighting conditions, something which renders detection difficult.

One reason that polishing roses arise is uneven pressure application which occurs in different movements when a rotating polishing drum or a polishing cloth is moved across the surface which is to be polished by the movement. Grinding, rubbing, and other forms of rotating or oscillating finishing processes may also cause polishing roses.

Unsatisfactorily often, polishing roses are not discovered until the finished vehicle is subjected to bright sunlight, and the roses are then visible only when the polished surface is observed at a certain angle. The problem is more evident for vehicles which have been painted in dark shades than for light-color painted vehicles since the polishing roses are more prominent on dark surfaces than on light surfaces. Since the majority of stations in a production process are indoors, and that is where testing for such surface defects would be best accomplished, it has been difficult to determine the presence of polishing roses before the vehicle has been fully assembled and able to be driven outside for ocular inspection. Accordingly, it is very difficult to continuously check the polishing result of individual sheet metal components before assembly.

Therefore, it is evident that there has long been a need for a reproducible and quantifiable measurement method for evaluating the presence of polishing roses or other similar surface defects of polished, or in otherwise finished components. Such a measurement method should further be insensitive to the light conditions which prevail at the testing station, and should be able to distinguish polishing roses from surface defects of other types which do not originate from the surface finishing.

In view of the above described deficiencies associated with methods and devices for inspecting, analyzing and identifying defects in polished surfaces, the present invention has been developed to alleviate these drawbacks and provide further benefits to the user. These enhancements and benefits are described in greater detail hereinbelow with respect to several alternative embodiments of the present invention.

DISCLOSURE OF THE INVENTION

The present invention in its several disclosed embodiments alleviates the drawbacks described above with respect to conventional methods and devices for inspecting, analyzing and identifying defects in polished surfaces and incorporates several additionally beneficial features.

Accordingly, an object of the present invention is to provide a method and a device for measuring and quantifying surface defects on a test or finished surface by means of optical registration with subsequent image analysis and/or image processing. This object may be achieved by and through methods and devices that are constructed and operated according to the invention as described herein, and equivalents thereto.

The method according to the present invention includes recording at least two partial images with at least one camera during illumination of a test surface with light from a spot lighting source or from a light source for parallel light that is oriented in such a way that the angle of incidence of the light in relation to the location of the recording camera or cameras is different for different partial images. Thereafter, the recorded partial images are processed in a central unit wherein a difference image is created by means of calculating the difference between different partial images. In this way, the intensity of the manufactured difference image is proportional to the degree of surface defect on the test surface. For example, a camera or equivalent imaging device (for example an electronic CCD-camera) may be used to photograph a surface of interest under illumination using a first light source for one image, and thereafter using a second light source for a second image. Subsequently, the two obtained partial images are image-processed in an image analyzer. By example, this may be accomplished by subtracting one partial image from the other and using this subtracted image (or difference image), it is possible to separate the polishing roses from other surface defects which do not originate from the surface treatment operation.

The ability to make this type of analysis stems from the use of the alternating light sources, each having a different angle of incidence which causes an optical phenomenon that manifests itself as the visible polishing roses to appear to be displaced backwards and forwards when they are illuminated in turn by the different light sources. Other occurring defects, however, originating for example from the paint or the sheet metal appear to remain immobile. This phenomenon makes it possible to separate the polishing roses from other surface defects, which of course is of great importance to locating the reason for a possible quality problem.

When practicing the invention, the measurement arrangement of the device of the present invention may be varied in several different ways, as long as the angle of incidence, when illuminating the test surface, is different for different partial images.

Accordingly, the measurement arrangement may include, for example, the use of one single light source, but two cameras. Similar effects can be obtained from the use of one light source and two images from the same camera, but with the camera in two different positions with respect to the target surface for each of the two images.

Another alternative measurement arrangement uses a mobile light source which is displaced between different positions in order to obtain different angles of incidence for the light when recording different partial images. In such cases, the mobile light source is preferably combined with a single stationary camera, but may also be combined with one or several different stationary or mobile cameras used for the image taking.

The light sources are advantageously arranged in pairs or in groups of more than two and illuminate the test surface laterally; that is, at an angle which can vary between zero and ninety degrees. By using several lamp groups, the test surface may alternatingly be illuminated from several different angles in a horizontal direction, enabling the test surface to be illuminated from several different directions without being turned or rotated.

Under certain conditions, however, it may be necessary or desirable to move or rotate the test surface between different partial images. In such cases, when recording different partial images, different light angles of incidence may be obtained by means of displacing the test surface, instead of displacing the camera or the light source, or by using several cameras or light sources in different positions. The displacement or rotation can be achieved by means of any previously known movement inducing mechanisms.

It has been found that the light which is reflected from the polishing roses may be polarized, which in such cases facilitates the detection.

When recording partial images, the camera or cameras are advantageously placed directly above the test surface which is to be measured. The camera(s) are preferably focused on the polishing roses, which often do not have the plane of the image in the plane of the test surface.

Independently of which measurement arrangement is used, the light source and the camera may be calibrated by means of placing a diffuse surface (e.g. white paper) in the intended position of the test surface.

Different image modifying units may be utilized that include lens systems, polarizers and colour filters which cause the polishing roses to appear more clearly on the partial images and, thereby, on the final difference image. Optical filtration with colour filters can, for example, be used in order to improve the signal/noise-ratio of the recorded images.

The camera or cameras are preferably electronic cameras such as CCD-cameras. A camera which is to be used when practicing the invention can be provided with two apertures on each side of the optical axis. This can be done by blocking the lens surface in a suitable way so that two image-registration apertures remain through which two images may be recorded simultaneously. A camera which has been equipped in this way with two apertures for recording images only requires the use of one light source, which is the also case when two separate cameras are used.

The intensity of light from the light sources, the time of exposure and aperture configuration can be adapted or controlled in order to provide images with a suitable exposure image. By utilizing pulsating light sources and short times of exposure, the influence of possibly disturbing light from the surroundings can be minimized. Further, by using carefully adapted settings, as described above, difference images with a sufficiently high resolution to make it possible to detect the occurrence of possible polishing roses can be obtained.

After having obtained a difference image by means of an image processing as described above, the image analyzer calculates a surface area A, essentially corresponding to the size of the polishing rose or roses which have been detected in the image window. The total defect area may, for example, be determined as the sum of all surfaces for which the measured light intensity exceeds a certain threshold value. Also, more complicated mathematical formulas or equations can be used in order to estimate the extent of the surface defects.

Furthermore, the image analyzer is made to calculate a measure of the intensity of the polishing rose or polishing roses lev which corresponds to the sum of the light effect within the defect area. By means of inserting the parameters A and lev in an empirically developed formula, a "mark" is obtained. The empirical formula has been obtained by means of adapting measurement values, which have been obtained by means of the method according to the invention, to marks which have been obtained by means of conventional manual, visual assessment. The marks which are obtained in this way have proved to correlate very well with the results from manual, visual assessment.

The reflectance variation, which is dependent on different intrinsic reflectance of different colors, requires a compensation method for different colors if comparable results shall be obtained.

The angle of observation of the camera or cameras is essential to enabling the empirical formula to provide marks which correlate with manual, visual assessment. The suitable angle of observation has to be arrived at by trial on location at each testing station.

Trials have shown for example, that when measuring on polished surfaces which have been painted with metallic paints, there is a maximum allowed angle of observation if it is to be possible to identify polishing roses with the empirical formula. When the angle of observation exceeds the allowed value, the measurement result is heavily impaired since so-called metallic flakes are projected on the difference images.

There are several methods of increasing the resolution and definition of the partial images, and thereby also the clarity of the final difference images which are to be used for measuring and quantifying possible polishing roses.

Accordingly, by means of image processing in an image analyzer according to known methods and apparatus, a background image, i.e. an image which has been recorded with the light source switched off, can be subtracted from each partial image.

Each partial image can also be adjusted with respect to amplification, based on a calibration image for the prevailing combination of camera/light source, or in another way be signal-processed, with the aim of increasing the detection degree of surface defects before the production of difference images.

Also, difference images which have been obtained by means of subtraction between different partial images may be image-processed in different ways in order to further enhance the polishing roses. Thus, by means of so-called correlation techniques, polishing roses which appear at slightly different coordinates in different partial images can be clarified. Smaller defects such as "spots" and the like can be removed with median filters.

The above-mentioned empirical formula or algorithm, which is used in order to calculate a mark may instead be constituted of an adapting neuronal net or other mathematic equations.

Accordingly, the present invention provides a reproducible method and device for measuring and quantifying surface defects, such as polishing roses, which method, in addition, is essentially insensitive to the light conditions which prevail at the time of measurement.

The beneficial effects described above apply generally to the exemplary methods and devices for inspecting, analyzing and identifying defects in polished surfaces disclosed herein. The specific structures through which these benefits are delivered will be described in detail hereinbelow.

BRIEF DESCRIPTION OF THE DRAWINGS

The invention will now be described in greater detail in the following way, by example only, and with reference to the attached drawings, in which.

MODE(S) FOR CARRYING OUT THE INVENTION

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Figure 1:
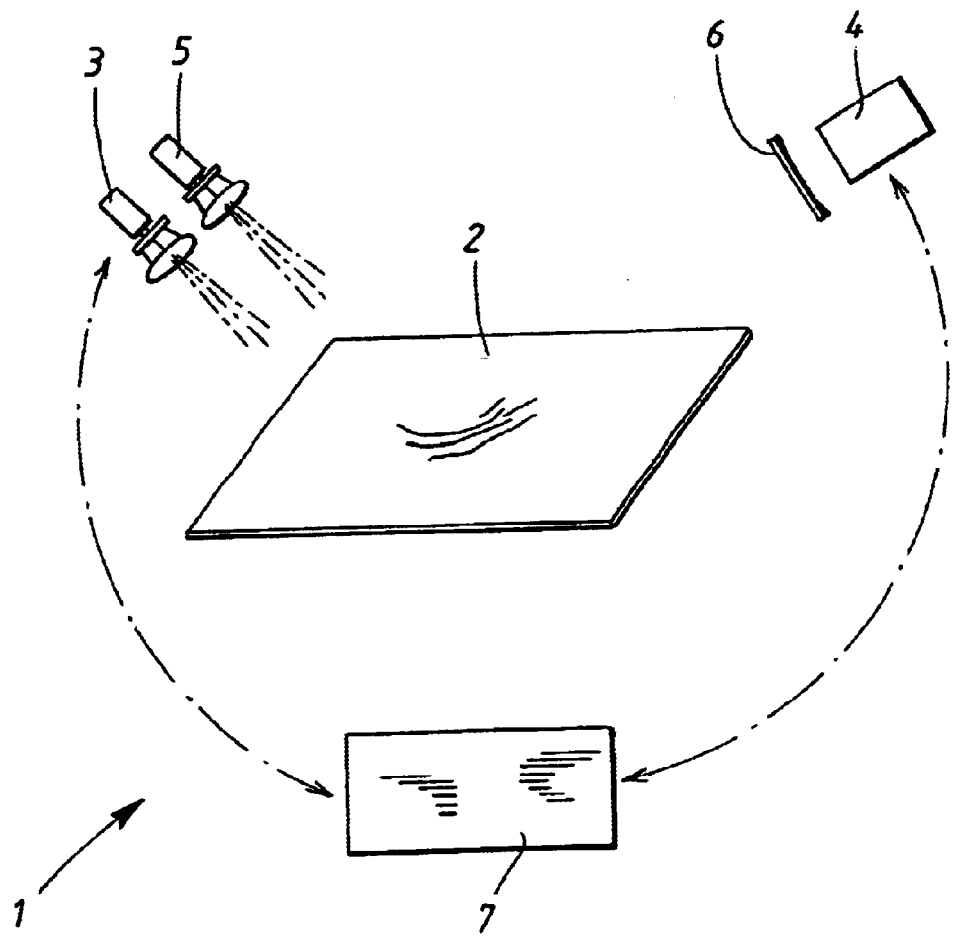
FIG. 1 schematically illustrates a preferred embodiment of a device according to the invention.

Referring to FIG. 1, a preferred embodiment of the arrangement or device 1 according to the present invention is shown, and by means of which the method of the present invention may be practiced. The method according to the invention comprises first illuminating a test surface 2 with parallel light from a first spot lighting source 3 at the same time as a camera 4, preferably an electronic camera, records a first image of the test surface 2. Thereafter, the first spot lighting source 3 is switched off and a second spot lighting source 5, adjacent to and parallel to the first spot lighting source 3, illuminates the test surface 2 at the same time as the camera 4 records a second image of the test surface 2. The camera 4 is advantageously provided with an image modifying unit 6, which may include image altering lenses, filters, polarizers or other elements which may facilitate subsequent image processing.

The first and second images are transferred to a central unit 7 that includes image analysis functions and control functions. Both the spot lighting sources 3 and 5 and the camera 4 are controlled by the central unit 7. At the central unit 7, the second image is subtracted from the first image (or vice versa) by image processing in order to provide a difference image. In the difference image, surface defects, such as polishing roses, appear with a certain intensity corresponding to the degree of severity of the surface defects being analyzed. The central unit 7 is advantageously arranged so that, when evaluating an obtained difference image, the central unit 7 is able to provide both a measure of the area of the surface defects, and a measure of the intensity of the surface defects, as has been earlier described.

Figure 2:
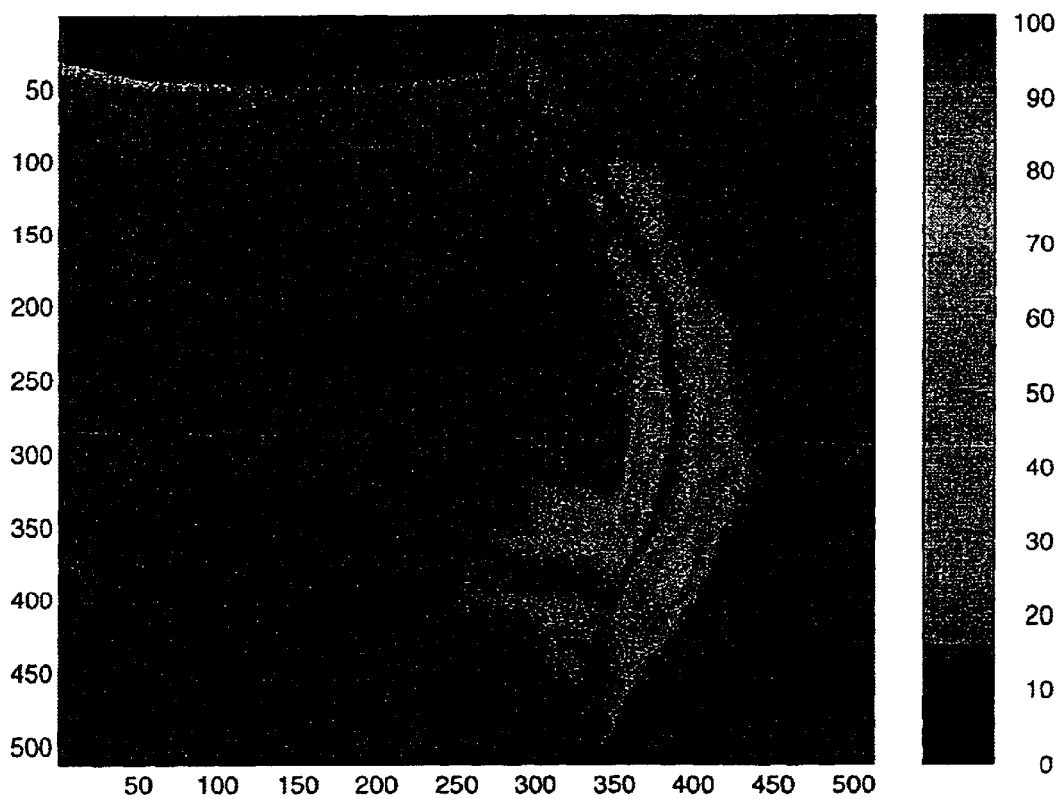
FIG. 2 shows a difference image obtained by means of the method according to the present invention.

FIG. 2 shows an example of a difference image which has been obtained by means of the method and the device according to the disclosed invention. The illustrated difference image should only be regarded as an example, however, and such a difference image can, with previously known techniques, be visualized and clarified in many ways.

The equipment whose arrangement constitutes the present invention are known to persons skilled in the art, and each component in itself is commercially available. This availability does not, however, imply that the inventive concept which is the basis of the present invention is known. In fact, the opposite is true; even though the components for constructing an embodiment of the present invention are and have been readily available, still no one in the art has conceived of the inventive arrangement and method of utilization disclosed herein for inspecting, analyzing and identifying defects in polished surfaces.

The present invention is in no way limited to being performed according to the above-mentioned embodiments, or to what is shown in the attached drawings, but may be varied within the scope of the attached claims.

Accordingly, the camera or cameras used are not necessarily of an electronic type, such as a video camera (CCD), but it is also conceivable to photograph different partial images using a conventional camera and light sensitive film, and thereafter to scan these partial images into an image analyzer for separate image processing.

What is claimed and desired to be secured by Letters Patent is as follows:

1. A method for measuring and quantifying surface finishing defects on a coated opaque test surface, said method comprising:
   utilizing at least one light source, at least one camera, and a central unit that has image analysis capability;
   recording at least two partial images with said at least one camera while illuminating the opaque test surface using said at least one light source, wherein the at least two partial images are produced from the test surface by differing the angle of incident light for different partial images;
   processing the at least two partial images by said central unit, thereby establishing a difference image from said at least two partial images; and
   analyzing said difference image to quantify the degree of surface finishing defects on the coated opaque test surface.

2. The method as recited in claim 1 wherein said central unit further has operational control capabilities over at least one of said at least one light source and said at least one camera.

3. The method as recited in claim 1 wherein the test surface, upon recording of the first partial image, is illuminated by the light source placed in a first position, and said test surface, when recording the second partial image, is illuminated by the light source placed in a second position.

4. The method as recited in claim 1 wherein the first partial image of the test surface is recorded by the camera placed in a first position and the second partial image of said test surface is recorded by the camera placed in a second position.

5. The method as recited in claim 1 wherein said central unit provides a measure of an area of the surface defect and a measure of the intensity of the surface defect from said difference image.

6. The method as recited in claim 1 further comprising:
   producing a surface defect on the test surface to be quantified by treating the test surface utilizing a treatment process selected from the group of polishing, rubbing and grinding.

7. The method as recited in claim 1 further comprising:
   moving a position of the test surface between the recording of said at least two partial images.

8. The method as recited in claim 1 further comprising:
   recording simultaneously a plurality of partial images utilizing a plurality of image registration apertures in said camera.

9. The method as recited in claim 1 further comprising:
   utilizing an image modifying device when recording a partial image in order to facilitate subsequent image processing of said partial image.

10. The method as recited in claim 1 further comprising:
    selecting an image modifying device from the group comprising optical lenses, filters, and polarizers.

11. An arrangement for measuring and quantifying surface finishing defects on a coated opaque test surface, said arrangement comprising:
    at least one light source, at least one camera, and a central unit that has image analysis capabilities and control capabilities;
    said at least one camera and said at least one light source being configured for recording at least two partial images while illuminating the opaque test surface using said at least one light source, wherein the at least two partial images are produced from the test surface by differing the angle of incident light for different partial images;
    said central unit being arranged for producing a difference image by subtracting one of said at least two partial images while illuminating the opaque test surface using said at least one light source;
    said central unit having a capability to measure an area of the surface finishing defect and to measure an intensity of the surface finishing defect from said difference image.

12. The arrangement as recited in claim 11 further comprising:
    said at least one light source having a first angle of incidence when a first of said at least two partial images is recorded; and
    said at least one light source having a second angle of incidence when a second of said at least two partial images is recorded.

13. The arrangement as recited in claim 11 further comprising:
    at least one image modifying unit, said image modifying unit selected from the group comprising optical lenses, filters, and polarizers that facilitate a subsequent image processing of said partial image.

14. The arrangement as recited in claim 11 further comprising:
    a motion inducing mechanism for changing the position of the test surface between recording said at least two partial images.

15. The arrangement as recited in claim 11 wherein said camera further comprises:

a plurality of image registration apertures through which a plurality of partial images are recorded, each of said plurality of partial images being recorded through each of said plurality of image registration apertures and each of said plurality of partial images having a different angle of incidence with respect to said test surface.

16. A method for identifying surface finishing defects on a painted opaque surface of an automobile part, said method comprising:

providing an automobile part having a painted opaque surface to be exposed on an incorporating assembled vehicle;

recording a first partial image of an area of interest on said painted opaque surface desired to be tested for surface defects that become apparent under high intensity lighting;

combining said first partial image with a second partial image of the area of interest thereby forming a difference image, wherein the first and second partial images are produced from the opaque surface by differing the angle of incident light for each partial images; and analyzing said difference image to identify indicators in said difference image of surface defects in said painted opaque surface.

17. The method as recited in claim 16 further comprising:

utilizing at least one light source, at least one camera, and a central unit that has image analysis capabilities for making said first and second partial images and analyzing said first and second partial images to identify surface defects in said painted opaque surface.

18. The method as recited in claim 16 further comprising:

comparing said difference image with known representations of surface defects for identifying similarities therebetween indicative of surface defects in said painted surface.

* * * * *